US012788354B2

(12) United States Patent
Nishijima et al.

(10) Patent No.: US 12,788,354 B2
(45) Date of Patent: Nov. 10, 2026

(54) MOBILE RADIOGRAPHIC IMAGING APPARATUS, STORAGE MEDIUM, AND WIRELESS COMMUNICATION METHOD

(71) Applicant: Konica Minolta, Inc., Tokyo (JP)

(72) Inventors: Yuuichi Nishijima, Mitaka (JP); Atsushi Taneda, Koganei (JP); Naoki Hayashi, Higashimurayama (JP)

(73) Assignee: KONICA MINOLTA, INC., Tokyo (JP)

( * ) Notice: Subject to any disclaimer, the term of this patent is extended or adjusted under 35 U.S.C. 154(b) by 68 days.

(21) Appl. No.: 19/059,364

(22) Filed: Feb. 21, 2025

(65) Prior Publication Data

US 2025/0204882 A1 Jun. 26, 2025

Related U.S. Application Data

(63) Continuation of application No. 17/899,064, filed on Aug. 30, 2022, now Pat. No. 12,257,099.

(30) Foreign Application Priority Data

Aug. 30, 2021 (JP) ................................ 2021-139782

(51) Int. Cl.
*A61B 6/00* (2024.01)

(52) U.S. Cl.
CPC ............ *A61B 6/563* (2013.01); *A61B 6/4405* (2013.01)

(58) Field of Classification Search
CPC .............................. A61B 6/4405; A61B 6/563
See application file for complete search history.

(56) References Cited

U.S. PATENT DOCUMENTS 12,127,868 B2 10/2024 Nukanobu
2009/0278051 A1* 11/2009 Ohara .................... A61B 6/563 250/370.09

(Continued)

FOREIGN PATENT DOCUMENTS

JP 5428767 B2 2/2014
JP 2016028628 A 3/2016

(Continued)

OTHER PUBLICATIONS

JPO Notice of Reasons for Refusal for corresponding JP Application No. 2021-139782; Issued on Feb. 1, 2022.

(Continued)

*Primary Examiner* — Blake C Riddick
(74) *Attorney, Agent, or Firm* — CANTOR COLBURN LLP

(57) ABSTRACT

A mobile radiographic imaging apparatus that performs dynamic imaging by using radiation, includes a detector, a wireless communication interface, and a hardware processor. The detector detects a first wireless access point and a second wireless access point. The wireless communication interface connects to the first wireless access point as a connection point and outputs a dynamic image including a plurality of frames acquired in the dynamic imaging to the first wireless access point. The hardware processor controls a change of the connection point from the first wireless access point to the second wireless access point. The hardware processor further performs control to inhibit the change of the connection point in a period when the frame images are still being output to the first wireless access point.

7 Claims, 6 Drawing Sheets

(56) References Cited

U.S. PATENT DOCUMENTS

| | | | | |
|---|---|---|---|---|
| 2012/0045991 | A1* | 2/2012 | Nonaka | H04W 76/10 455/41.2 |
| 2012/0228499 | A1* | 9/2012 | Koyanagi | G03B 42/04 250/336.1 |
| 2013/0094628 | A1* | 4/2013 | Lalena | A61B 6/4283 378/98 |
| 2013/0129048 | A1* | 5/2013 | Chicchetti | A61B 6/4405 378/62 |
| 2013/0188629 | A1* | 7/2013 | Lemaire | A61B 5/0013 370/338 |
| 2014/0177798 | A1* | 6/2014 | Kitagawa | A61B 6/4233 378/62 |
| 2014/0292777 | A1* | 10/2014 | Kudo | A61B 6/461 345/520 |
| 2014/0369459 | A1* | 12/2014 | Foos | A61B 6/025 378/4 |
| 2015/0078522 | A1* | 3/2015 | Makino | A61B 6/4405 378/96 |
| 2015/0078527 | A1* | 3/2015 | Iwamoto | A61B 6/4283 378/91 |
| 2015/0078529 | A1* | 3/2015 | Tsubota | A61B 6/4405 378/91 |
| 2016/0015341 | A1* | 1/2016 | Lee | A61B 6/42 250/336.1 |
| 2016/0220217 | A1* | 8/2016 | Uchiyama | A61B 6/42 |
| 2016/0295094 | A1* | 10/2016 | Endoh | A61B 6/548 |
| 2017/0227660 | A1* | 8/2017 | Zhang | H04W 12/50 |
| 2017/0265834 | A1* | 9/2017 | Saigusa | A61B 6/545 |
| 2018/0160286 | A1* | 6/2018 | Oh | H04N 1/00127 |
| 2018/0317874 | A1* | 11/2018 | Kudou | A61B 6/4283 |
| 2018/0368797 | A1* | 12/2018 | Kuwata | A61B 6/5217 |
| 2018/0368801 | A1* | 12/2018 | Allen | A61B 6/4283 |
| 2019/0166585 | A1* | 5/2019 | Proano | A61B 6/4233 |
| 2020/0155109 | A1* | 5/2020 | Garcia | A61B 6/4208 |
| 2020/0229780 | A1* | 7/2020 | Kim | A61B 6/4208 |
| 2022/0183639 | A1* | 6/2022 | Nukanobu | A61B 6/486 |
| 2023/0062154 | A1 | 3/2023 | Nishijima et al. | |
| 2023/0252635 | A1 | 8/2023 | Hasegawa et al. | |
| 2023/0284989 | A1 | 9/2023 | Nishijima et al. | |
| 2023/0404516 | A1 | 12/2023 | Fukazu et al. | |

FOREIGN PATENT DOCUMENTS

| | | | |
|---|---|---|---|
| JP | 2017094007 | A | 6/2017 |
| JP | 2019076638 | A | 5/2019 |
| WO | 2020213564 | A1 | 10/2020 |

OTHER PUBLICATIONS

USPTO Notice of Allowance for corresponding U.S. Appl. No. 17/899,064 dated Nov. 21, 2024.

SIPO First Office Action for corresponding CN Application No. 202211050711.0 issued May 19, 2026.

* cited by examiner

MOBILE RADIOGRAPHIC IMAGING APPARATUS, STORAGE MEDIUM, AND WIRELESS COMMUNICATION METHOD

CROSS-REFERENCE TO RELATED APPLICATIONS

The present application is a continuation application of U.S. patent application Ser. No. 17/899,064, filed on Aug. 30, 2022, the entire contents of which are incorporated herein by reference. The Ser. No. 17/899,064 application claims the benefit of the date of the earlier filed Japanese Patent Application No. 2021-139782 filed on Aug. 30, 2021, priority of which is also claimed herein, and the entire contents of which are incorporated herein by reference.

BACKGROUND

Technological Field

The present invention relates to a mobile radiographic imaging apparatus, s storage medium, and a wireless communication method.

Description of the Related Art

Conventionally, various technologies have been proposed regarding wireless communication in medical facilities. For example, JP 2017-94007A discloses, for the purpose of improving the stability of AEC (automatic exposure control) in a wireless communication environment, checking the stability for each radio frequency band prior to imaging and selecting a stable frequency band.

JP 5428767 B2 discloses calculation and grasp of a wireless communication status (speed) in wireless communication from the radiographic image generator to the control device in advance, and instructions to change the communication channel or communication standard when there is a problem with the communication status.

SUMMARY

As described above, the conventional technologies mainly relate to selection of the wireless communication standard and frequency band to be used for sending and receiving control information and image data based on the state of wireless communication before imaging. However, with the introduction of a dynamic imaging using a mobile radiographic imaging apparatus, it is no longer possible to ensure stable wireless communication by the completion of image output by simply selecting the communication standard, frequency band, etc. to be used based on the state prior to imaging.

For example, an existing wireless LAN environment in a medical facility is suitable for electronic medical record terminals, assuming use in a fixed location and a small amount of transferred data (for example, IP addresses separated by floor or room, and the wireless standard 11b/g, etc., which has a slow transfer rate). During transfer of image data taken by a mobile radiographic imaging apparatus in such an environment, disconnection from a wireless network (switching of wireless access points) occurs due to due to movement peculiar to the mobile radiographic imaging apparatus. However, short sending time does not affect transfer of a still image, which has been conventionally mainly transferred.

However, output of a dynamic image requires a longer time than output of a still image because all of the several hundred frame images captured at one time are output to a dynamic analyzer or the like via wireless communication. This increases the rate of disconnection from the wireless network before completion of the image output and thus the rate at which resending of data is required. Specifically, for example, when a mobile radiographic imaging apparatus that is connected to one wireless access point and outputting dynamic images is moved to the next patient to be imaged, in response to detection of another wireless access point with stronger wireless communication strength at the mobile radiographic imaging apparatus, the access point is switched to the other wireless access point before all the frame images have been output. In such a case, the dynamic image has to be sent again from the beginning in accordance with the DICOM (Digital Image and Communications in Medicine) communication standard, which requires one file to be communicated per one access, resulting in a further delay in the completion of image output. JP 2017-94007A and JP 5428767 B2 do not take these points into consideration at all.

The present invention was made in view of the above problems and aims to suppress delay in output of a dynamic image due to disconnection of wireless communication caused by movement of the mobile radiographic imaging apparatus and resending of the data.

To achieve at least one of the abovementioned objects, according to an aspect of the present invention, there is provided a mobile radiographic imaging apparatus that performs dynamic imaging by using radiation, including:

a detector that detects a first wireless access point and a second wireless access point;

a wireless communication interface that connects to the first wireless access point as a connection point and outputs a dynamic image including a plurality of frames acquired in the dynamic imaging to the first wireless access point; and a hardware processor that controls a change of the connection point from the first wireless access point to the second wireless access point, wherein the hardware processor performs control to inhibit the change of the connection point in a period when the frame images are still being output to the first wireless access point.

To achieve at least one of the abovementioned objects, according to an aspect of the present invention, there is provided a non-transitory computer-readable storage medium storing a wireless communication program for a computer provided in a mobile radiographic imaging apparatus including a detector and a wireless communication interface that performs dynamic imaging by using radiation, the wireless communication program causing the computer to perform:

causing the detector to detect a first wireless access point and a second wireless access point and a second wireless access point;

causing the wireless communication interface to connect to the first wireless access point as a connection point and to output a dynamic image including a plurality of frames acquired by the dynamic imaging to the first wireless access point; and controlling a change of the connection point from the first wireless access point to the second wireless access point, wherein, in the controlling, the change of the connection point is inhibited in a period when the frame images continue to be output to the first wireless access point.

To achieve at least one of the abovementioned objects, according to an aspect of the present invention, there is provided a wireless communication method to perform wireless communication for a mobile radiographic imaging apparatus including a detector and a wireless communication interface that performs dynamic imaging by using radiation, including:

causing the detector to detect a first wireless access point and a second wireless access point and a second wireless access point;

causing the wireless communication interface to connect to the first wireless access point as a connection point and to output a dynamic image including a plurality of frames acquired by the dynamic imaging to the first wireless access point; and controlling a change of the connection point from the first wireless access point to the second wireless access point, wherein, in the controlling, the change of the connection point is inhibited in a period when the frame images continue to be output to the first wireless access point.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION OF THE EMBODIMENTS

Hereinafter, one or more embodiments of the invention will be described with reference to the drawings. However, the scope of the invention is not limited to the disclosed embodiments.

(Configuration of Radiographic Imaging System 100)

First, the configuration of the embodiment of the present invention will be described.

Figure 1:
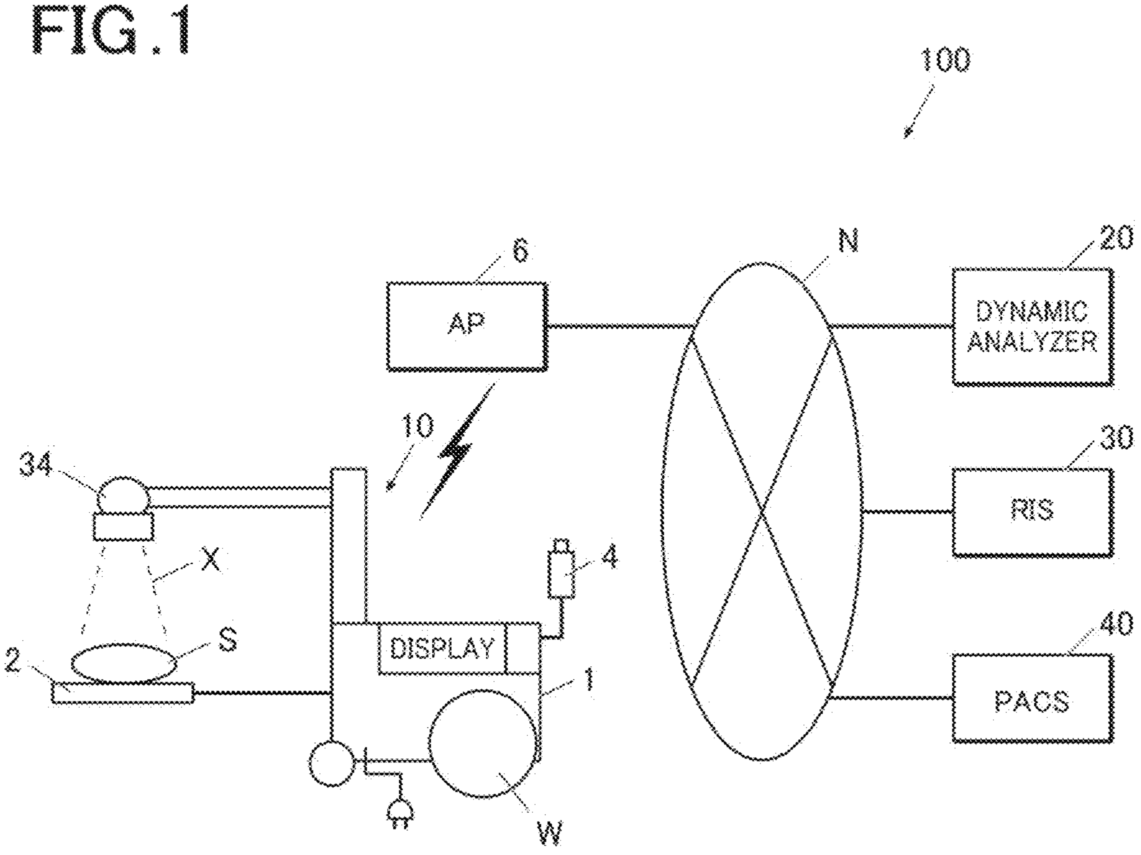
FIG. 1 shows an example of an overall configuration of a radiographic imaging system.

FIG. 1 shows an example of an overall configuration of a radiographic imaging system 100 in the present embodiment. The radiographic imaging system 100 is a system built in a medical facility, and as shown in FIG. 1, includes a mobile radiographic imaging apparatus 10, a dynamic analyzer 20, a RIS (Radiology Information System) 30, and a PACS (Picture Archiving and Communication System) 40 which are connected to each other to enable data transmission and reception via a communication network N such as LAN (Local Area Network), WAN (Wide Area Network), etc. There are multiple wireless access points (APs) 6 in the medical facility where the radiographic imaging system 100 is set up. The plurality of wireless access points 6 differ from each other, for example, in communication standards, channels, and/or IP addresses. The mobile radiographic imaging apparatus 10 can be connected to the communication network N via the wireless access points 6.

The devices constituting the radiographic imaging system 100 are each based on the DICOM (Digital Image and Communications in Medicine) standard, and communication between the devices is performed in accordance with DICOM.

The mobile radiographic imaging apparatus 10 is a device for performing radiographic imaging of a patient who is, for example, difficult to move around in a round-the-clock visit. The mobile radiographic imaging apparatus 10 has wheel(s) W on the main body 1 and is configured as a movable medical vehicle. The mobile radiographic imaging apparatus 10 may be a portable apparatus that does not have wheels.

The mobile radiographic imaging apparatus 10 is brought into an operating room, intensive care unit (ICU), hospital room, or the like. While a Flat Panel Detector (FPD) 2 is inserted, for example, between a subject S lying on a bed and the bed or in an insertion port on the opposite side of the bed from the subject S (not shown), radiation is emitted from the radiation source 34 to capture a still or a dynamic image of the subject S. In the present system, still imaging refers to acquiring a single image of the subject S in response to a single imaging operation. Dynamic imaging refers to acquiring a plurality of images of the subject S in response to a single imaging operation by repeatedly irradiating the subject S with radiation such as X-rays in pulse form at predetermined time intervals (pulse irradiation) or continuously irradiating the subject S at a low dose rate without interruption (continuous irradiation). A series of images acquired by dynamic imaging is called a dynamic image. Each of the plurality of images constituting the dynamic image is called a frame image.

Here, dynamic imaging includes taking a moving image, but does not include capturing a still image while displaying a moving image.

Figure 2:
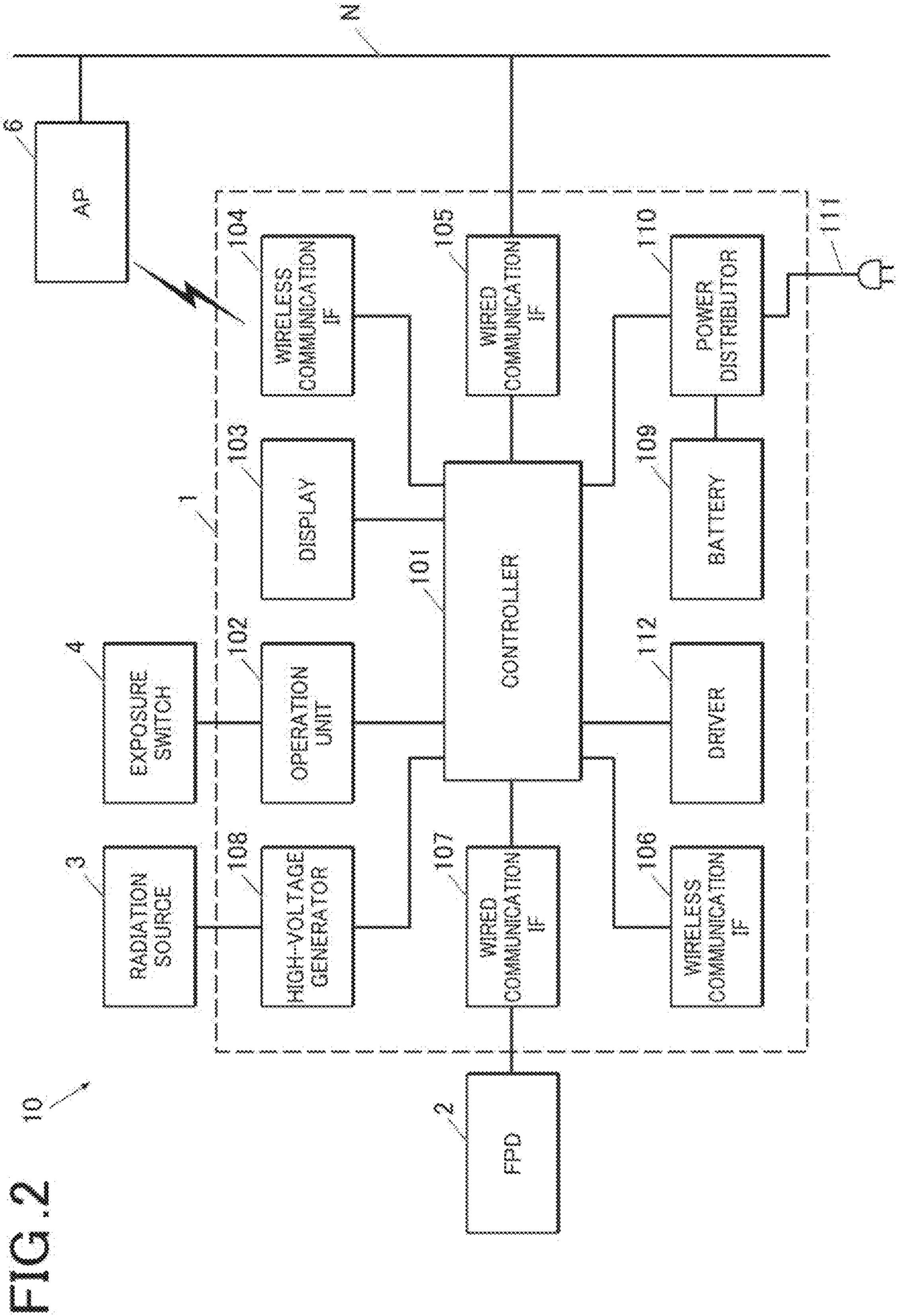
FIG. 2 is a block diagram showing a functional configuration of the mobile radiographic imaging apparatus in FIG. 1.

FIG. 2 is a block diagram showing a functional configuration of the mobile radiographic imaging apparatus 10.

As shown in FIG. 2, the mobile radiographic imaging apparatus 10 includes a main body 1, an FPD 2, a radiation source 3, an exposure switch 4, and the like.

The main body 1 includes a controller (hardware processor) 101, an operation unit 102, a display 103, a wireless communication IF 104, a wired communication IF 105, a wireless communication IF 106, a wired communication IF 107, a high-voltage generator 108, a battery 109, a power distributor 110, and the like.

The controller 101 includes a CPU (Central Processing Unit), a RAM (Random Access Memory), a ROM (Read Only Memory), and the like. The CPU of the controller 101 reads various programs stored in the ROM, loads the programs into the RAM, and performs various processes in accordance with the loaded programs. The CPU of the controller 311 thus centrally controls operation of the components of the mobile radiographic imaging apparatus 10.

The operation unit 102 includes operation buttons, a touch panel, and the like, and detects user operations (type of operation button pressed, position of finger or touch pen contact, and the like) and outputs them as operation information to the controller 101.

In addition, an exposure switch 4 is connected to the operation unit 102 for the user instructions to emit radiation X.

The exposure switch 4 may be connected to the mobile radiographic imaging apparatus 10 by wire or wirelessly and may be used for remote control. In this way, the user can control radiation exposure from a position remote from the main body 1 of the mobile radiographic imaging apparatus 10.

The display 103 includes a monitor such as a liquid crystal display (LCD) or a cathode ray tube (CRT), and displays examination order information, a captured image, and the like in accordance with commands of display signals input by the controller 101. The examination order information is sent from the RIS 30, for example, and includes examination identification information (such as examination ID), examination date, patient information on the patient to be the subject S (patient ID, name, gender, age, hospital room (hospital ward), and the like), information on each imaging performed in the examination (imaging ID, imaging type indicating whether the image is acquired by still imaging or dynamic imaging, an imaging condition (for example, imaging part, imaging direction, frame rate, number of images, imaging time, irradiation power of the radiation source 3, and the like), type of analysis process to be performed by the dynamic analyzer 20 (such as type or name of analysis process), requesting department, classification as emergency or non-emergency.

A sub-monitor separates from the display 103 may be connected by wire or wirelessly.

The wireless communication IF (wireless communication interface) 104 is an interface that wirelessly connects to the wireless access point 6 and sends and receives (inputs and outputs) data to and from an external device(s) (such as the dynamic analyzer 20 and the RIS 30) connected to the communication network N via the wireless access point 6. The wireless communication IF 104 receives radio waves from the wireless access point 6 and detects the wireless access point 6 as a detector. The wireless communication IF 104 also acquires the signal strength of the received radio waves.

The wired communication IF 105 is an interface that connects to the communication network N by wired communication with its communication cable plugged therein, and sends and receives data to and from an external device (s) connected to the communication network N. The connection to the communication network N can be switched to wired connection or wireless connection based on a control signal by the controller 101.

The wireless communication IF 106 is a wireless interface that sends and receives data to and from the FPD 2 by wireless communication.

The wired communication IF 107 is an interface that sends and receives data to and from the FPD 2 by wired communication with its communication cable plugged therein.

The connection to the FPD 2 can be switched to wired connection or wireless connection based on the control signal by the controller 101.

The high voltage generator 108 applies a voltage to the radiation source 3 in accordance with the preset radiation irradiation conditions (imaging type of dynamic imaging or still imaging, conditions related to radiation irradiation such as tube voltage, tube current, irradiation time, current-time product, and the like) based on the control signal received from the controller 101.

The battery 109 is configured to supply the power stored in it to the power distributor 110 and to store the power supplied by the power distributor 110.

The power distributor 110 has a power cable 111 with a plug at its tip, and is configured to receive power supply from an external source with the plug plugged into a nearby power outlet. The power distributor 110 is configured to distribute the power supplied from the battery 109 or an external source to various components of the mobile radiographic imaging apparatus 10.

The driver 112 is a drive circuit for driving a motor to rotate the wheels W. Based on a control signal from the controller 101, the driver drives the motor to rotate the wheels W.

The FPD 2 includes a radiation detector that generates electric charges depending on the radiation dose upon exposure to radiation X, a substrate with a two-dimensional (matrix) array of pixels with switch elements for storing and releasing electric charges, a readout circuit that reads out the amount of electric charges emitted from each pixel as a signal value, a controller that generates image data from a plurality of signal values read out by the readout circuit, a communication unit that sends image data and various signals to the main body 1 by wire or wirelessly, a connector into which a cable is inserted for connection to the main body 1, and the like.

The FPD 2 may be a so-called indirect type FPD that incorporates a scintillator or the like, converts the received radiation X into light of other wavelengths, such as visible light, with the scintillator, and generates electric charges according to the converted light. Alternatively, the FPD 2 may be a so-called direct type FPD that generates electric charges directly from radiation X without a scintillator or the like.

The radiation source 3 includes, for example, a rotating anode, a filament, and the like (not shown in the drawing). When voltage is applied from the high-voltage generator 108, the filament emits an electron beam depending on the voltage toward the rotating anode, and the rotating anode generates radiation X at a dose corresponding to the intensity of the electron beam.

The dynamic analyzer 20 performs an analysis process on the dynamic image output from the mobile radiographic imaging apparatus 10 and sends the dynamic image and analysis results to the PACS 40. The dynamic analyzer 20 can perform multiple types of analysis processes and performs a designated type of analysis process among the multiple types of analysis processes.

The RIS 30 is an order issuing device that issues and stores examination order information and sends the issued examination order information to the mobile radiographic imaging apparatus 10 via the communication network N.

The PACS 40 is an image management device that stores and manages medical images (still and dynamic images) generated by modalities such as the mobile radiographic imaging apparatus 10 and the analysis results by the dynamic analyzer 20, which are associated with patient and examination information.

(Operation)

Next, operations of the mobile radiographic imaging apparatus 10 will be described.

In the following description, the mobile radiographic imaging apparatus 10 communicates with an external device connected to the communication network N by wireless communication.

In the mobile radiographic imaging apparatus 10, upon receiving the examination order information from the RIS 30 via the wireless communication IF 104, the controller 101 stores the received examination order information in the RAM and displays it on the examination list screen (not shown) of the display 103. When the examination order information of an examination to be performed is selected in the examination list screen by the operation unit 102 and an instruction to start an examination is given, the controller 101 controls the high voltage generator 108 and the FPD 2 to perform imaging based on the selected examination order information. The FPD 2 sends the captured image acquired by imaging to the mobile radiographic imaging apparatus 10. When the imaging is completed, the controller 101 temporarily stores the captured image sent from the FPD 2 via the wireless communication IF 106 or the wired communication IF 107 in the RAM and starts outputting the captured image (transferring image data) via the wireless communication IF 105. When the dynamic imaging has been performed, the captured image is output to the dynamic analyzer 20, and when the still imaging has been performed, the image is output to the PACS 30.

Figure 3:
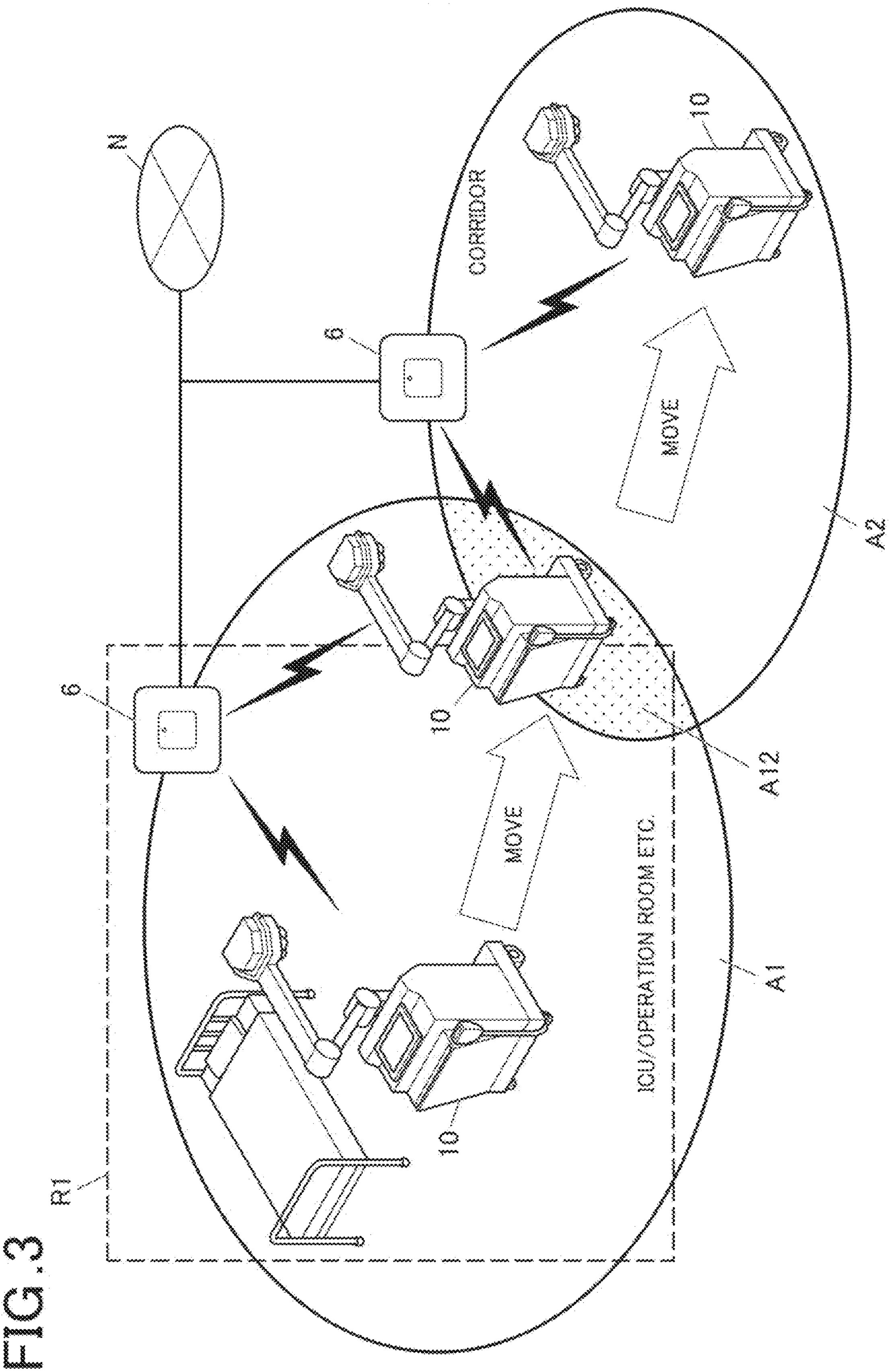
FIG. 3 schematically shows a wireless communication environment in a medical facility.

FIG. 3 schematically shows the wireless communication environment in a medical facility. As shown in FIG. 3, multiple wireless access points 6 of different types (for example, WLAN1 and WLAN2) are provided in the medical facility. Upon entering a communication area of one of the wireless access points 6 (for example, a communication area A1 of WLAN1 or a communication area A2 of WLAN2), the controller 101 of the mobile radiographic imaging apparatus 10 connects to the wireless access point 6 via the wireless communication IF 104 and performs wireless communication via this wireless access point 6 with an external device such as the RIS 30 and the dynamic analyzer 20. Upon moving into an area where the communication areas of a plurality of wireless access points 6 overlap (for example, an area A12 where areas A1 and A2 overlap), the controller 101 generally (in the conventional technology) causes the wireless communication IF 104 to switch (change) the connection to the wireless access point 6 with the strongest radio waves.

For example, as shown in FIG. 3, upon entering a room R1 such as an ICU/operating room, which is within the area A1, the mobile radiographic imaging apparatus 10 is connected to the WLAN1 via the wireless communication IF 104. After the radiographic imaging, an image is output via the connected WLAN1. When the mobile radiographic imaging apparatus 10 moves and enters the area A12 during the image output, where the signal strength of WLAN2 is stronger than that of WLAN1, generally (in the conventional technology), a connection point of the wireless communication IF 104 is switched to the WLAN2. However, since the DICOM standard requires communication of one file per one access, switching of the connection point to the WLAN2 during dynamic imaging requires, for example, re-sending several hundred frames of dynamic images from the beginning, which delays the completion of the image output.

Therefore, in the mobile radiographic imaging apparatus 10 of the present embodiment, the controller 101 executes an image output control process described later to control to inhibit a change of the wireless access point 6 to which wireless communication IF 104 is connected while a plurality of frame images (a plurality of frames) of the dynamic image continues to be output.

Figure 4:
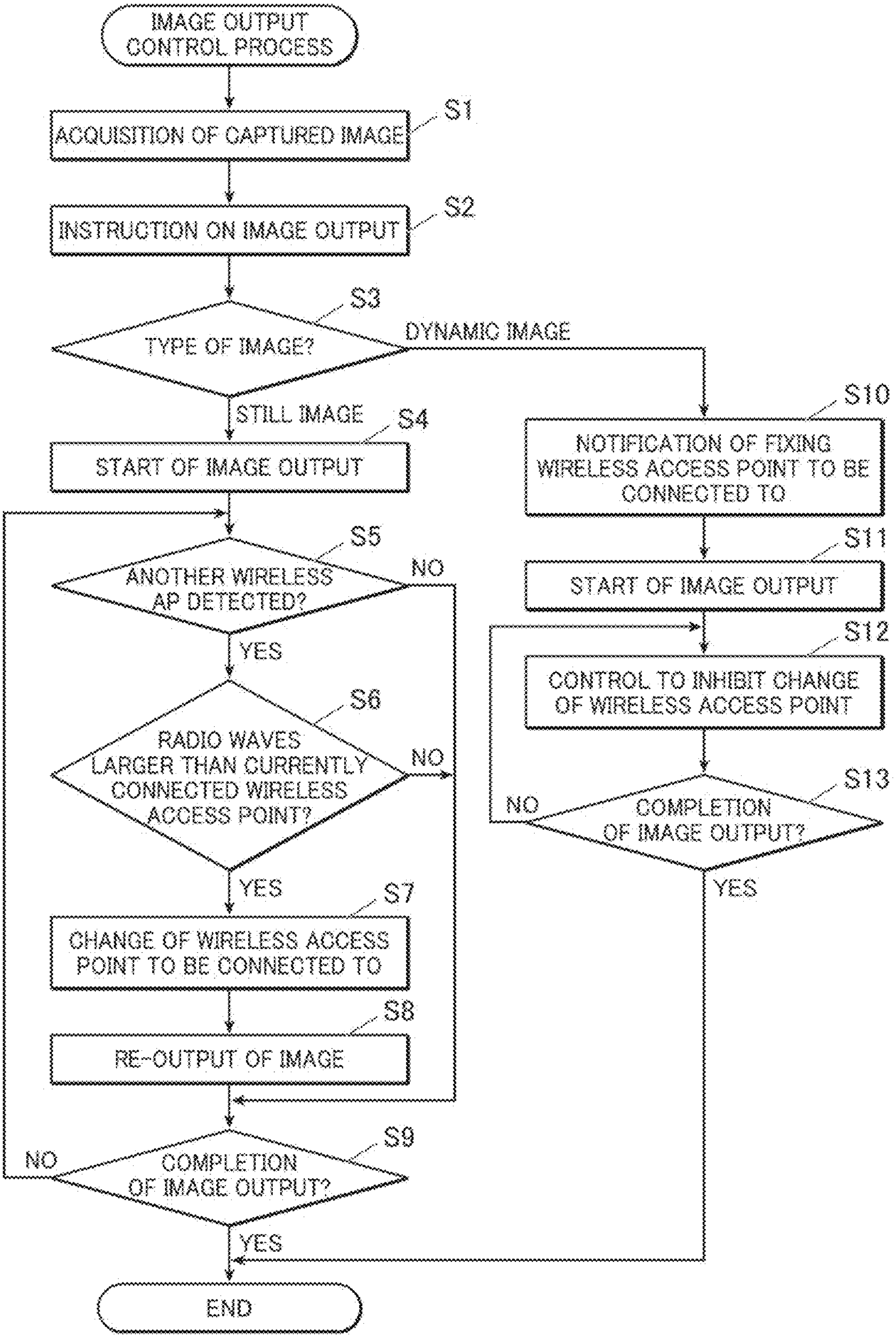
FIG. 4 is a flowchart showing the flow of the image output control process performed by the controller in FIG. 2.

FIG. 4 is a flowchart showing the flow of the image output control process. The image output control process is executed by the CPU of the controller 101 in cooperation with the program stored in ROM when imaging is started. Hereafter, the image output control process is described with reference to FIG. 4.

In the following, the wireless communication IF 104 is described as being connected to the wireless access point 6 with the strongest signal strength.

First, the controller 101 acquires the captured image from the FPD 2 by the wireless communication IF 106 or the wired communication IF 107 and temporarily store them in the RAM (Step S1).

Upon an instruction to output an image via the operation unit 102 (Step S2), the controller 101 determines whether the captured image is the still image or the dynamic image (Step S3).

In Step S3, for example, the type of image is determined based on the type of imaging in the examination order information.

Alternatively, without performing Step S2, the process by the controller 101 may automatically proceed to Step S3 when the imaging or examination is finished.

If the type of the captured image is determined to be the still image (Step S3; still image), the controller 101 causes the wireless communication IF 104 to start output of the captured image to the PACS 30 via the currently connected wireless access point (wireless AP) 6 (Step S4).

Next, the controller 101 determines whether the wireless communication IF 104 has detected a wireless access point 6 other than the currently connected wireless access point 6 (Step S5).

If it is determined that the wireless communication IF 104 has not detected any other wireless access point 6 (Step S5; NO), the process by the controller 101 proceeds to Step S9.

If it is determined that the wireless communication IF 104 has detected any other wireless access point 6 (Step S5; YES), the controller 101 determines whether the radio wave from the other wireless access point 6 is stronger than the radio wave from the wireless access point 6 connected to the wireless communication IF 104 (Step S6).

If it is determined that the radio wave from the other wireless access point 6 is lower than the radio wave strength from the currently connected wireless access point 6 (Step S6; NO), the process by the controller 101 proceeds to Step S9.

If it is determined that the radio wave from the other wireless access point 6 is stronger than the radio wave strength from the currently connected wireless access point 6 (Step S6; YES), the controller 101 changes the wireless access point 6 to which the wireless communication IF 104 is connected to the other wireless access point 6 (Step S7). Then, the controller 101 causes the wireless communication IF 104 to output the captured image again (Step S8), and the process proceeds to Step S9.

In Step S9, the controller 101 determines whether or not the output of the captured image is completed (Step S9).

If it is determined that the output of the captured image is not completed (Step S9; NO), process of the controller 101 returns to Step S5.

If it is determined that the output of the captured image is completed (Step S9; YES), the controller 101 finishes the image output control process.

On the other hand, if the type of the captured image is determined to be the dynamic image (Step S3; dynamic image), the controller 101 causes the display 103 to display notification information of fixing the connection point of the wireless communication IF 104 to the currently connected wireless access point 6 (referred to as the first wireless access point) (Step S10).

Figure 5:
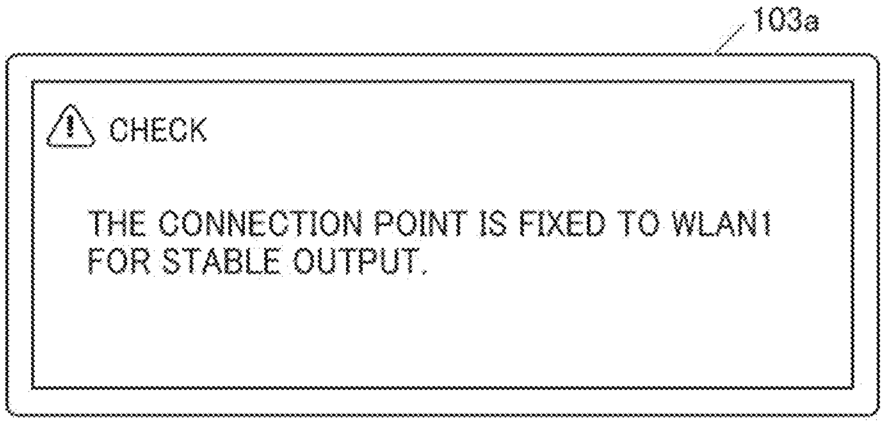
FIG. 5 shows an example of notification information displayed on a display in Step S10 in FIG. 4.

FIG. 5 shows an example of the notification information displayed on the display 103 in Step S10. In the example described here, the WLAN1 is the first wireless access point. As shown in FIG. 5, in Step S10, for example, a dialog box 103*a* displaying notification information such as "The connection point is fixed to WLAN1 for stable output" is displayed.

As a result, the user can be notified that the connection point is fixed to the WLAN1 and urged to refrain from moving the mobile radiographic imaging apparatus 10.

Next, the controller 101 causes the wireless communication IF 104 to start outputting the captured image (dynamic image) to the dynamic analyzer 20 via the first wireless access point (Step S11), and then performs the control to inhibit the change of the wireless access point 6 to which the connection is made (Step S12). In other words, during the output period of the frame images of the dynamic image, the controller 101 controls the wireless access point 6 connected to the wireless communication IF 104 to remain the first wireless access point 6. As a result, the connection point of the wireless communication IF 104 is fixed to the first wireless access point to which it is currently connected.

In Step S12, even if the wireless communication IF 104 detects another wireless access point 6 (called a second wireless access point) that is different from the first wireless access point, for example, the controller 101 controls the wireless communication IF 104 not to change its connection point to the second wireless access point while the frame images of the dynamic image continue to be output. For example, even if the radio wave from the first wireless access point is weaker than the radio wave from the second wireless access point, during output period of the frame images of the dynamic image, the wireless communication IF 104 is controlled not to change its connection point to the second wireless access point.

Alternatively, the controller 101 may perform invalidation of the detection of the second wireless access point by the wireless communication IF 104 during the output period of the frame images of the dynamic image, so that the wireless access point 6 to which the wireless communication IF 104 is connected is not changed from the first wireless access point. For example, the controller 101 may control, during the output period of the frame images of the dynamic image, the wireless communication IF 104 such that it does not detect any other wireless access point (the second wireless access point)(for example, such that the wireless communication IF 104 does not receive radio waves from the second wireless access point). Alternatively, even if the wireless communication IF 104 outputs information indicating detection of the second wireless access point to the controller 101, the controller 101 may ignore the information (or treat the information indicating no detection).

Figure 6:
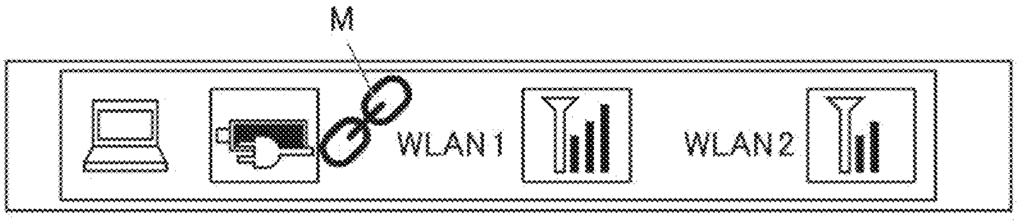
FIG. 6 shows an example of notification information displayed during the control to inhibit a change of the wireless access point.

During the control to inhibit the change of the wireless access point 6, the controller 101 may display notification information on the display screen of the display 103 that notifies the user that the connection point is fixed, and which wireless access point is the first wireless access point that is fixed as the connection point. For example, as shown in FIG. 6, the names (WLAN1, WLAN2, etc.) of the wireless access points 6 currently detected by the wireless communication IF 104 and icons indicating the respective radio wave status are displayed in a predetermined area on the display screen of the display 103, and a mark M is displayed on the name of the fixed first wireless access point indicating fixed connection point. This allows the user to recognize that the wireless access point to be connected to is fixed and the fixed connection point.

Figure 7:
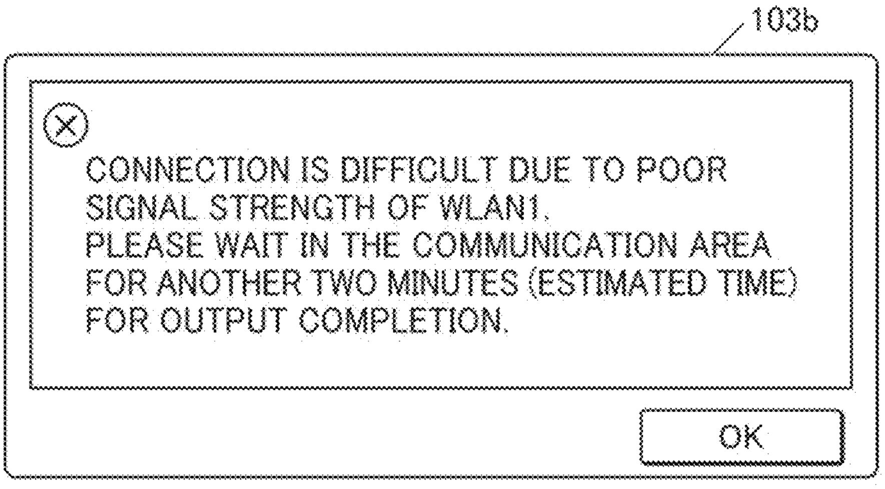
FIG. 7 shows an example of notification information to notify the user that the radio wave from the first wireless access point is weakening.

When the radio wave strength from the first wireless access point drops below a predetermined threshold value, as shown in FIG. 7, the controller 101 preferably displays a dialog box 103*b* on the display 103 displaying notification to the user that the radio wave from the first wireless access point is weakening, a message that urges the user to wait within the communication area of the first wireless access point until the image output is completed, and an estimate of the waiting time. This allows the user to recognize that it is better to wait without moving to avoid delays in the image output and the waiting time, thereby preventing communication disconnections and resending.

If the connection to the first wireless access point is lost, for example, by the user moving the mobile radiographic imaging apparatus 10, the controller 101 causes the wireless communication IF 104 to connect to the second wireless access point and resend the dynamic images.

If all the frame images of the dynamic image have not yet been output (Step S13; NO), the controller 101 performs the process of Step S12.

If all the frame images of the dynamic image have been output (Step S13; YES), the controller 101 finishes the image output control process.

Thus, in the image output control process, during the output period of the frame images of the dynamic image, changing the wireless access point 6 to which the wireless communication IF 104 connects is inhibited.

Therefore, it is possible to suppress the delay in the output of the dynamic image due to disconnection of wireless communication and resending resulting from switching of the wireless access point 6 due to movement of the mobile radiographic imaging apparatus 10.

(Modified Example)

Hereinafter, a modified example of the above embodiment will be described.

In the control to inhibit the change of the wireless access point 6 to which the wireless communication IF 104 is connected in Step S12 of the above image output control process, the controller 101 may control the driving system not to operate. The driving system rotates the wheels W to move the mobile radiographic imaging apparatus 10. For example, the controller 101 controls the above driving system not to operate when the radio wave from the first wireless access point is below a predetermined threshold value. For example, the controller 101 controls the driver 112 not to drive the motor that rotates the wheels W to lock and prevent the wheels W from rotating. Alternatively, the controller 101 may control the driver 112 so as to reduce the rotational rate of the wheels W. This can prevent the mobile radiographic imaging apparatus 10 from moving, so that changing the wireless access point 6 to which the wireless communication IF 104 is connected can be inhibited.

In the examples of the embodiment shown above, the information on stop of changing the wireless access point is output on the display screen of display 103 as a notifier and includes the characters shown in FIG. 5 and FIG. 7 and the figures (icons, marks, and designs) shown in FIG. 6, which do not limit the present invention. The information on stop of changing the wireless access point is information for notifying the user that the changing of the wireless access point to be connected to is inhibited, information for urging the user to refrain from moving the apparatus, and the like and includes at least one of: information on the first wireless access point that is fixed (has been fixed) as the connection point (FIG. 5 to FIG. 7 etc.); information on the second wireless access point that is different from the first wireless access point and detected during the image output; and comparison of the information on the first wireless access point with the information on the second wireless access point.

Information on the first wireless access point includes, for example, the following information. Here, WLAN1 is an example of the name of the first wireless access point.

Information on the first wireless access point to be fixed (before connection or before fixation)

Example: "The connection point will now be fixed to WLAN 1", the dialog box 103*a* in FIG. 5

Information on the first wireless access point that is fixed (after fixation)

Example: "The fixed connection point is WLAN1", the icon in FIG. 6

Information that the first wireless access point is scheduled to be fixed

Example: "The connection point is scheduled to be fixed to WLAN 1."

Information that the first wireless access point is in a fixed state (status)

Example: "The connection point is fixed to WLAN1", the icon in FIG. 6

Information on release of the fixation to the first wireless access point (time until release of the fixation (time until completion of the image output) and the like)

Example: "Connection point is fixed to WLAN1 for another XX minutes", "YY minutes left until completion of the image output/release", the dialog box 103*b* in FIG. 7

Information that the apparatus is out of the communication range of the first wireless access point Example: "The apparatus will soon be out of the communication range of WLAN 1", the dialog box 103*b* in FIG. 7

Strength of radio waves from the first wireless access point

Example: The icon in FIG. 6

Information on the second wireless access point includes, for example, the following information. Here, WLAN2 is an example of the name of the second wireless access point.

Information such as the name of the second wireless access point being detected

Example: "WLAN2 is detected, but the connection point is fixed to WLAN1", the icon in FIG. 6.

The time required to complete the image output if the connection point is switched to the second wireless access point (time required for switching the wireless access point and resending the data)

Strength of radio waves from the second wireless access point

Example: the icon in FIG. 6

The comparison of the information on the first wireless access point with the information on the second wireless access point includes, for example, comparison of the following information.

The required time to complete the image output when using the first wireless access point and the required time to complete the image output when using the second wireless access point (information on which one takes how much less required time)

Strength of radio waves from the first wireless access point and strength of radio waves from the second wireless access point The distance where communication with the first wireless access point is possible and the distance where communication with the second wireless access point is possible (maps illustrating respective communication areas and the like)

The method of outputting information on stop of changing the wireless access point is not limited to displaying the characters and figures described above, but can also be a notification using one or more of the following: a character (s), figure, color, light, sound, and vibration.

For example, the mobile radiographic imaging apparatus 10 may include a warning light as a notifier, such that the controller 101 causes the warning light to emit green light when strength the radio waves from the currently connected first wireless access point (fixed connection point) is more than a first threshold value, yellow light when the strength of the radio waves from the fixed connection point is equal to or less than the first threshold value and more than a second threshold, and red light when the strength of the radio waves from the fixed connection point is equal to or less than the second threshold value (the first threshold value>the second threshold value). Thus, the controller 101 can urge the user to refrain from moving the apparatus depending on the color of the light from the warning light, so that the connected wireless access point is not changed. Alternatively, the display color of the display screen may be changed depending on the strength of the radio wave from the first wireless access point.

For example, the mobile radiographic imaging apparatus 10 may include a speaker as the notifier, and the controller 101 may cause the speaker to output information on stop of changing the wireless access point as a voice or warning sound. For example, the message shown in FIG. 5 or FIG. 7 may be output by voice. Alternatively, when the strength of the radio wave from the currently connected first wireless access point falls to below a predetermined threshold value, the controller 101 may cause the speaker to output a voice message indicating the fact or to output a warning sound.

For example, the mobile radiographic imaging apparatus 10 may include a vibration device as the notifier, and the controller 101 may cause the vibration device to output information on stop of changing the wireless access point as vibration. For example, when the strength of the radio wave from the currently connected first wireless access point falls to below a predetermined threshold value, the controller 101 may cause the vibration device to output vibration.

In the examples of the embodiment described above, during the image output, the connection point is fixed to the currently connected first wireless access point, and the change of the wireless access point is inhibited. However, depending on the wireless communication standards (communication speed) of the first wireless access point and the second wireless access point, switching the connection point to the second wireless access point may result in a shorter time required to complete the image output. For example, if WLAN1 in FIG. 3 is of a standard with a slow communication speed (for example, IEEE802.11b), WLAN2 is a standard with a high communication speed (for example, IEEE802), and the apparatus enters the area A12, switching the connection point to the second wireless access point may result in a shorter time required to complete the image output even taking into account the time required for disconnection and reconnection.

Figure 8:
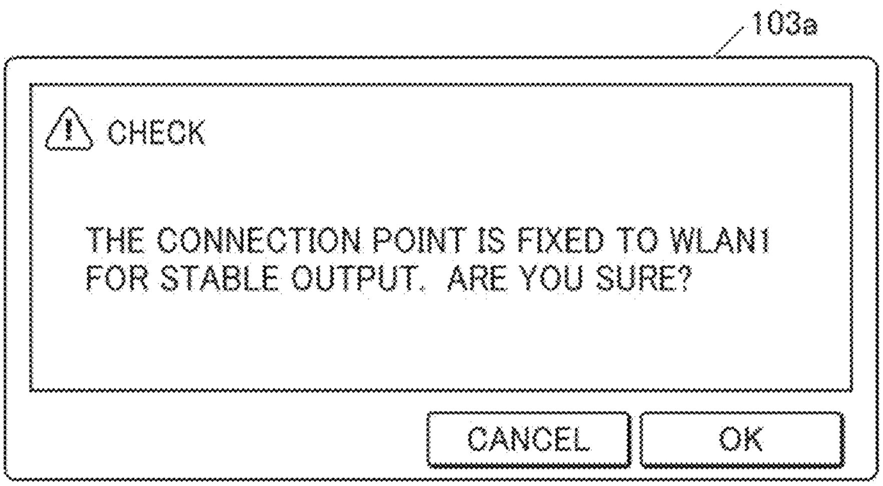
FIG. 8 shows an example of notification information where a user can select whether or not to perform the control to inhibit the change of the wireless access point.

Therefore, whether or not to perform the control to inhibit the change of the wireless access point 6 may be configured to be selected by the user. For example, as shown in FIG. 8, an OK button and a CANCEL button may be displayed in the dialog box 103*a* displaying that the wireless access point 6 to which the wireless communication IF 104 is connected is to be fixed. Then, if the CANCEL button has been pressed, the control to inhibit the change of the wireless access point 6 is not performed after the image output is started, and the processes in Steps S6 to S10, which are executed when the type of the captured image is the still image, may be performed.

As a result, when the communication speed of the wireless access point to be fixed is known to be slow in advance, for example, the output of the dynamic image can be prevented from being delayed due to the control to inhibit the change of the wireless access point.

The controller 101 may store information such as arrangement of the wireless access points 6 in the medical facility and the communication speed of them in a storage such as the ROM or the RAM, and, in response to user operation, cause the display 103 to display such information as reference information to help the user decide whether to accept or reject the fixation. Alternatively, when a plurality of wireless access points 6 are detected, the controller 101 may calculate, compare, and display the communication speeds, time periods required to complete the image output, and the like for the respective wireless access points 6.

Alternatively, when the second wireless access point is detected during the control to inhibit the change of the wireless access point, the controller 101 may display an operation button or the like in order to receive instructions to change the connection point to the second wireless access point (or to stop the control to inhibit the change (to release the fixation)), while comparing the radio wave strengths, communication speeds, and time periods required to complete the image output, and the like for the first wireless access point and the second wireless access point, and displaying them on the display 103. Then, in response to the pressing of the operation button by the user, the connection point may be changed to the second wireless access point.

Alternatively, the control to inhibit the change may be inhibited (fixation may be released) upon detection of a connection to the wired communication IF 105.

As a result, it is possible to suppress the delay in the output of the dynamic image due to the control to inhibit the change of the wireless access point.

Alternatively, when the second wireless access point is detected during the control to inhibit the change of the wireless access point, the controller 101 may compare the radio wave strengths (or communication speeds, required time periods to complete the image output, etc.) from the first wireless access point and the second wireless access point. When the comparison result satisfies a predetermined condition, the controller 101 may automatically release the control to inhibit the change and change the connection point to the second wireless access point. For example, when the strength of the radio waves from the second wireless access point is larger than the strength of the radio waves from the first wireless access point by a predetermined value or more, when the communication speed of the second wireless access point is faster than the communication speed of the first wireless access point by a predetermined value or more, or when the time required to complete the image output via the second wireless access point is shorter than the time required to complete the image output via the first wireless access point by a predetermined value or more, the controller 101 automatically releases the control to inhibit the change and automatically changes the connection point to the second wireless access point.

As a result, it is possible to suppress the delay in the output of the dynamic image due to the control to inhibit the change of the wireless access point.

Whether or not to perform the control to inhibit the change of the wireless access point (whether or not to fix the connection point) may be configured to be designated by the user for each examination (or depending on where to visit, requesting department, etc.). For example, the control to inhibit the change of the wireless access point need not to be performed in an examination performed in an operating room, because the captured dynamic image is sequentially displayed on the spot for confirmation and thus may be output with a delay. However, in an examination in a ward round or in an emergency, it is necessary to complete the image output as soon as possible. Thus, the control to inhibit the change can be performed only, when necessary, by allowing the user to designate whether or not to perform the control to inhibit the change of the wireless access point.

The control to inhibit the change of the wireless access point is performed during the entire period when the frame images of the dynamic image are being output in the above embodiment, however, the control to inhibit the change of the wireless access point may be performed only during a part of the period. For example, if only a part of the frame images of a dynamic image is used for dynamic analysis, the control to inhibit the change of the wireless access point may be performed while the part of the frame images necessary for dynamic analysis are output, and the control to inhibit the change of the wireless access point may be released while the rest of the frame images are output.

In the above embodiment, whether or not to perform the control to inhibit the change of the wireless access point is determined based on whether the output target is a dynamic image or a still image, however, it may be explicitly designated by the user. For example, if the user designates the control to inhibit the change of the wireless access point prior to successive imaging (dynamic or still imaging) in a hospital ward crowded with a plurality of access points, output processes can be performed successively via a single connection point without being affected by other access points.

Although embodiments of the present invention and modifications thereof have been described above, the descriptions in the above embodiments and modifications are suitable examples of the present invention, and do not limit the present invention.

For example, the radiographic system 100 may include an electronic medical record system, and the mobile radiographic imaging apparatus 10 may be configured to output the still image and/or the dynamic image to the electronic medical record system via the communication network N.

Further, in the above, hard disks, nonvolatile semiconductor memories or the like are used as computer readable media of the programs of the present disclosure. However, this is not a limitation. As the computer readable media, portable storage media, such as CD-ROMs, can also be used. Further, as media to provide data of the programs of the present invention via communication lines, carrier waves can be used.

Although configurations and operations of the mobile radiographic imaging apparatus have been described and illustrated in detail, the disclosed embodiments are made for purposes of illustration and example only and not limitation.

The scope of the present invention should be interpreted by terms of the appended claims.

What is claimed is:

1. A mobile radiographic imaging apparatus that performs dynamic imaging by using radiation, comprising:

a detector that detects a first wireless access point and a second wireless access point;

a wireless communication interface that connects to the first wireless access point as a connection point and outputs a dynamic image including a plurality of frames acquired in the dynamic imaging to the first wireless access point; and a hardware processor that controls a change of the connection point from the first wireless access point to the second wireless access point, wherein in a period when frame images are still being output to the first wireless access point, the hardware processor performs a comparison between the first wireless access point and the second wireless access point and performs control to inhibit the change of the connection point based on a result of the comparison.

2. The mobile radiographic imaging apparatus according to claim 1, wherein the comparison includes a comparison of a wireless standard, and when the wireless standard of the first wireless access point provides a faster communication speed than the wireless standard of the second wireless access point, the hardware processor performs the control to inhibit the change of the connection point.

3. The mobile radiographic imaging apparatus according to claim 1, wherein the comparison includes a comparison of a strength of a radio wave, and when the strength of the radio wave from the first wireless access point is stronger than the strength of the radio wave from the second wireless access point, the hardware processor performs the control to inhibit the change of the connection point.

4. The mobile radiographic imaging apparatus according to claim 1, wherein when the second wireless access point is detected during the control to inhibit the change of the wireless access point, the hardware processor displays a comparison result, and in response to an input operation by a user, the connection point is changed to the second wireless access point.

5. The mobile radiographic imaging apparatus according to claim 4, wherein the hardware processor displays the comparison result while comparing radio wave strengths, communication speeds, or time periods required to complete an image output, for the first wireless access point and the second wireless access point.

6. The mobile radiographic imaging apparatus according to claim 4, wherein the input operation includes pressing an operation button by the user.

7. The mobile radiographic imaging apparatus according to claim 1, wherein in response to a user operation depending on an examination or a requesting department, the wireless access point is changed.

* * * * *